United States Patent [19]

Engl

[11] 4,275,598
[45] Jun. 30, 1981

[54] ULTRASONIC TESTING DEVICE

[75] Inventor: Günter Engl, Erlangen-Büchenbach, Fed. Rep. of Germany

[73] Assignee: Kraftwerk Union Aktiengesellschaft, Mülheim, Fed. Rep. of Germany

[21] Appl. No.: 117,862

[22] Filed: Feb. 4, 1980

Related U.S. Application Data

[63] Continuation of Ser. No. 923,382, Jul. 10, 1978, abandoned.

[30] Foreign Application Priority Data

Jul. 15, 1977 [DE] Fed. Rep. of Germany ....... 2732090

[51] Int. Cl.³ .......................................... G01N 29/04
[52] U.S. Cl. ..................................... 73/622; 73/640; 73/641
[58] Field of Search ................. 73/641, 640, 622, 624, 73/625, 628

[56] References Cited

U.S. PATENT DOCUMENTS

| | | | |
|---|---|---|---|
| 2,893,239 | 7/1959 | Renaut | 73/624 |
| 3,575,044 | 4/1971 | Gibbs et al. | 73/625 |
| 3,683,680 | 8/1972 | Johnson et al. | 73/628 |
| 3,712,119 | 1/1973 | Cross et al. | 73/625 |
| 3,921,440 | 11/1975 | Toth | 73/622 |
| 3,978,714 | 9/1976 | Shraiber et al. | 73/625 |

*Primary Examiner*—Anthony V. Ciarlante
*Attorney, Agent, or Firm*—Herbert L. Lerner

[57] ABSTRACT

Device for volumetric testing of pressure-vessel walls and pipes with a combined transmit-receive test head for scanning a test track having a given test-track spacing, includes an oscillator unit including an oscillating crystal and a receive oscillating crystal having respective centers spaced apart a distance smaller than that of the test-track spacing so that the test head has a full width within which at least one additional oscillating crystal is accommodated, the additional oscillating crystal being paired with one of the transmit and receive oscillating crystals so as to form therewith another oscillator unit including a transmit oscillating crystal and a receive oscillating crystal having centers spaced apart a distance smaller than that of the test-track spacing, the distance between the crystals of both of the oscillator units being substantially equal.

7 Claims, 14 Drawing Figures

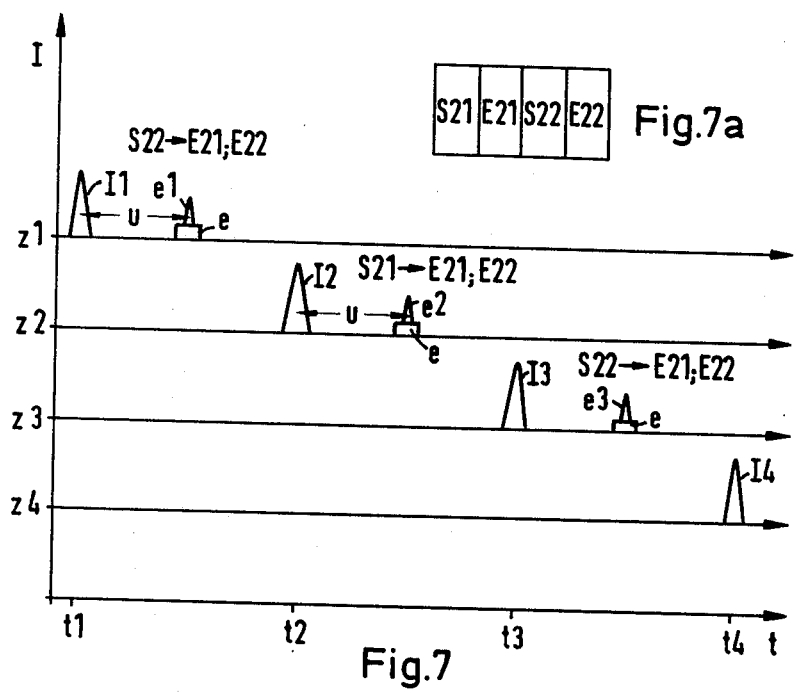

ULTRASONIC TESTING DEVICE

This is a continuation of application Ser. No. 923,382, filed July 10, 1978, now abandoned.

The invention relates to a device for volumetric testing of the walls of vessels and pipes and more particularly, to such a device for ultrasonic testing of welded seams and the heat-affected zones adjoining the welded seams in pressure vessels of nuclear reactors, with combined transmit-receive test heads (T-R Test heads) for scanning test tracks.

Such ultrasonic testing devices have become known heretofore, for example, from the journal "Materialpruefung" 17 (1975) No. 10, pages 347 to 352. According to guidelines of the German Reactor Safety Commission, the sensitivity calibration for repeat tests as detection limit is to be based, for the single-head technique, on the flat-bottom bore hole of 3 mm diameter and, for the tandem technique, on the flat-bottom bore hole of 10 mm diameter. This sensitivity must apply to the entire portion of the sound beam used for the test. This means that in the meander or sinuous scanning mode with defined test track spacing customary for repeat tests, this sensitivity adjustment must be made at the least sensitive point of the portion of the sound beam that is used i.e. with one-half the test track distance as the lateral offset. Due to the yet relatively narrow sound beam cross sections in the zones near the test head and the therewith associated steep energy drop for lateral offset, this can lead to difficulties if the heretofore known test heads are used with a wider test track spacing. The adjustment to the reference reflector at half the test track spacing can necessitate, due to the great sensitivity difference between the adjustment position and the central beam position, such a test sensitivity for the central beam that the latter indicates the structure noise far more strongly than would correspond to the detection limit on the basis of this adjustment process.

It is an object of the invention to provide an ultrasonic testing device of the type initially mentioned herein, by which the foregoing difficulties are elminated i.e. which exhibits also at half the test track spacing, a sufficient echo level of the adjustment reflector with a signal-to-noise margin which ensures satisfactory registration also in this range. This is to be attainable, especially, with the customary meander or sinuous test tracks having 20 mm testing spacing i.e. a reduction of the test track spacing should not be necessary.

A further or secondary object of the invention is to provide a test head for the ultrasonic test device of such construction that it can be used for single-head technique as well as for tandem technique and requires no test cycling over and above such cycling schemes as are known at present. It is a further object of the invention to provide such a test head having the same dimensions as the test heads that have been known heretofore.

With the foregoing and other objects in view, there is provided, in accordance with the invention, a device for volumetric testing of pressure-vessel walls and pipes with a combined transmit-receive test head for scanning a test track having a given test-track spacing, comprising an oscillator unit including an oscillating crystal and a receive oscillating crystal having respective centers spaced apart a distance smaller than that of the test-track spacing so that the test head has a full width within which at least one additional oscillating crystal is accommodated, the additional oscillating crystal being paired with one of the transmit and receive oscillating crystals so as to form therewith another oscillator unit including a transmit oscillating crystal and a receive oscillating crystal having centers spaced apart a distance smaller than that of the test-track spacing, the distance between the crystals of both of the oscillator units being substantially equal.

In accordance with another feature of the invention, all of the crystals are of equal width, which especially facilitates the manufacture and interchangeability of the test heads.

In accordance with a further feature of the invention, the test head is a three-oscillator test head, and the crystals include two simultaneously driven outer transmit oscillating crystals and a receive oscillating crystal disposed therebetween.

In accordance with an added feature of the invention, the test head is a three-oscillator test head, and the crystals include two outer receive oscillating crystals and a transmit oscillating crystal disposed therebetween and driven so as to be simultaneously received by the receive oscillating crystals.

In accordance with an additional feature of the invention, the test head is at least a three-oscillator test head and is operable for ultrasonic testing in a transmit-receive technique with longitudinal waves.

In accordance with yet another feature of the invention, the test head is at least a three-oscillator test head and is operable for ultrasonic testing in a transmit-receive technique with transverse waves.

In accordance with yet a further feature of the invention, the test head is at least a three-oscillator test head and is operable as a transmitter test head for ultrasonic testing in tandem technique, a receiver test head being associated with the transmitter test head.

In accordance with yet an added feature of the invention, the test head is at least a three-oscillator test head and is operable as a receiver test head for ultrasonic testing in tandem technique, a transmitter test head being associated with the receiver test head.

In accordance with a concomitant feature of the invention, the test head is at least a three-oscillator test head selectively drivable in transmitting and receiving functions, the oscillator units being alternatingly and sequentially drivable.

Features which are considered as characteristic for the invention are set forth in the appended claims.

Although the invention is illustrated and described herein as embodied in an ultrasonic testing device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which:

FIGS. 1a and 1b are a top plan and a side elevational view, respectively, of a conventional ultrasonic testing device with a transmit-receive test head and a test track spacing of the meander-shaped or sinuous test track of 20 mm;

in FIG. 1b, material defects in the form of vertically oriented reflectors are indicated in a region near the surface, the echo level of the adjusting reflector being represented in broken lines as a function of the lateral offset in FIG. 1a, as well as the material noise (shaded region);

FIGS. 2a and 2b are views similar to those of FIGS. 1a and 1b, respectively, of an embodiment of the ultrasonic testing device according to the invention; in FIG. 2a as in FIG. 1a, the echo level of the adjustment reflector being represented in broken lines as a function of the lateral offset, and also the material noise (shaded region) is also shown therein;

FIGS. 3a and 3b are enlarged views of plot diagrams corresponding to the plot diagrams shown in FIGS. 1a and 2a, respectively, the echo level of the adjusting reflector being plotted in dB on the ordinate thereof, and the lateral offset being plotted on the abscissa thereof, the FIGS. 3a and 3b, representing relationships for a test head with longitudinal transmit-receive technique (TRL) in a first depth zone, and being brought into relationship with the plot diagrams in FIGS. 4a and 4b, respectively, disposed in alignment therewith therebelow;

FIG. 7 is a plot diagram of a time variation of pulse amplitude in a time multiplex operation; and FIGS. 8 and 9 are tabulations of time-division multiplex operations with respect to the three and the four-oscillator test heads, respectively.

Figures 1A, 2A:
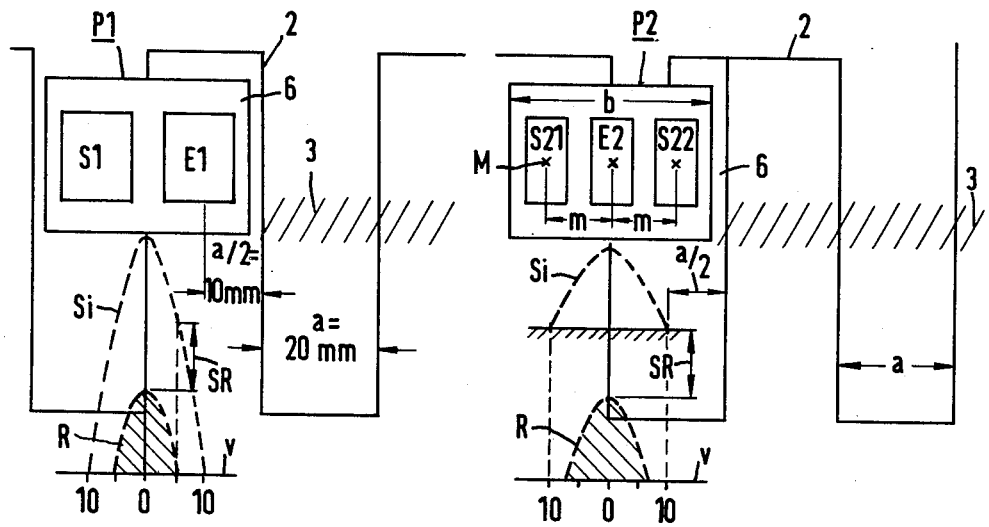
Figures 1B, 2B:
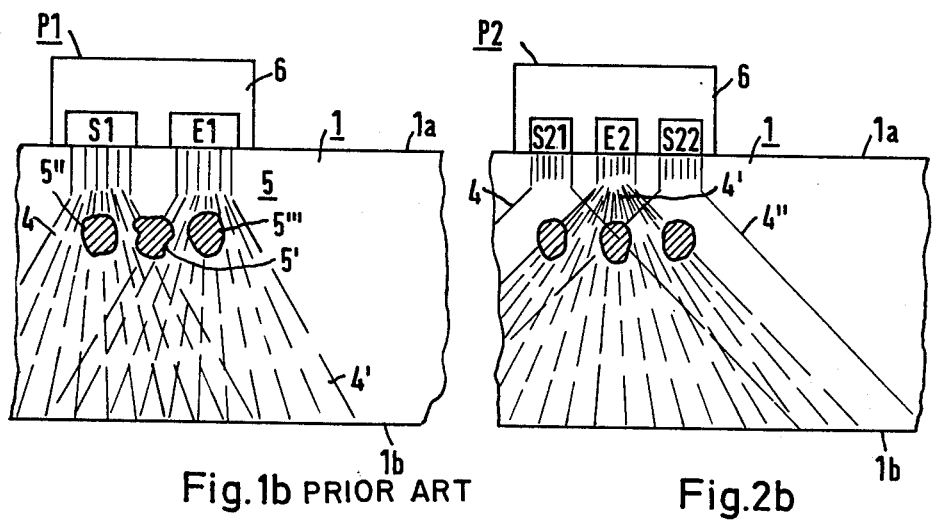

Referring now to the drawing and first, particularly, to FIGS. 1a and 1b, thereof, there is shown a conventional transmit-receive (T-R) test head P1 which can be moved along a meander-shaped or sinuous test track 2 having a test track spacing of a=20 mm. The test head P1 is disposed in test position on the casing surface 1a of an otherwise non-illustrated reactor pressure vessel. The region of a weld 3 and the adjoining heat-affected zones are subjected to a penetrating ultrasonic beam 4, which starts from any oscillating transmitter crystal S1, is reflected at a lower boundary-forming surface 1b, and returns, in part, to an oscillating or vibrating receiver crystal E1. From the sound beam 4', it is apparent that the crystal E1 can also operate as the transmitter and, accordingly, the crystal S1 then assumes the receiver function. Through an evaluation of the returning receive signals, which is effected by means of a recorder or an oscillographic device or by means of computers, conclusions can be drawn as to material defects contained within the wall e.g. a vertically oriented reflector 5. Three positions 5', 5", 5''' of the reflector 5 relative to the test heads S1 and E1 or the test tract 2 are shown; the middle position 5' being the most favorable whereas, relatively, the outer positions 5" and 5''' are the most unfavorable. The oscillating or vibrating crystals S1 and E1 are accommodated in a housing 6, not shown in detail, which is supported, preferably in gimbals, inside the test head mounting of a non-illustrated manipulator. As is shown by the curve Si (echo level of an adjusting reflector), plotted as a function of the lateral offset v, the echo level has dropped below the noise level R at half the test track spacing (10 mm) whereas, for a lateral offset of 5 mm, the signal-to-noise spacing SR remains available yet. A lesser or tighter test track spacing of 10 mm with a maximum lateral offset of 5 mm, however, means a considerably increased testing effort, which is avoided in accordance with the invention by the novel test head construction, which is explained in greater detail hereinafter with reference to FIGS. 2a and 2b.

In regard to the test head P2, the distance m between the centers M of two adjacent transmitting and receiving vibrating or oscillating crystals S21, E2, on the one hand, and E2, S22, on the other hand, is chosen smaller than the test track spacing a and so dimensioned that, as in the instant case, another vibration or oscillating crystal S21 or S22 can be accommodated within the full width b of the test head P2, which corresponds to the width of the test head P1 and, in fact, with substantially the same spacings m between the centers M of the respective adjacent crystals S21, E2, S22. These vibrating crystals S21, E2 and S22 preferably have the same widths. The illustrated embodiment of FIGS. 2a and 2b is a preferred embodiment according to the invention since the same dimensions are attainable therewith, for a diameter of the crystals that is yet justifiable, as are attainable in the case of the test head P1. As is readily apparent, two simultaneously driven outer transmit crystals S21 and S22 are provided, and one receive crystal E2 disposed in the middle therebetween. As shown in FIG. 2b, the crystals S21, E2, S22 produce ultrasonic beam cones 4, 4' and 4", respectively. In FIG. 2a, the echo level Si of an adjustment reflector is again plotted qualitatively as a function of the lateral offset v. A comparison with FIG. 1a shows that, for a lateral offset a/2, in the instant case equal to 10 mm, a considerably higher useful signal is obtainable, the signal-to-noise margin SR of which is, relative to the structure noise R, about as large as the margin SR according to FIG. 1a for a lateral offset of 5 mm. The reason for this is due, especially, to a considerably better sensitivity distribution, as a comparison of FIGS. 1b and 2b will show and as will be explained further hereinbelow. Also in this regard, the functions of the transmit and receive signals are interchangeable, so that the sequence might also be E21-S2-E22.

Figure 3A:
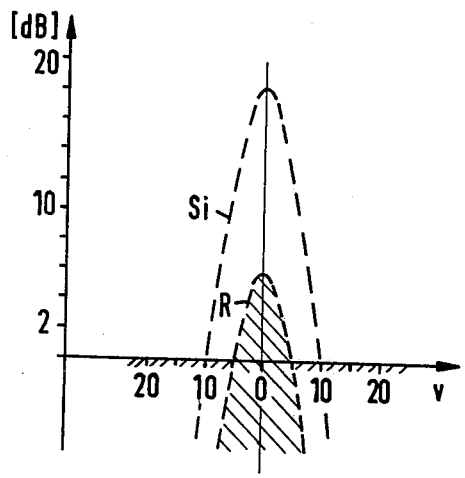
Figure 3B:
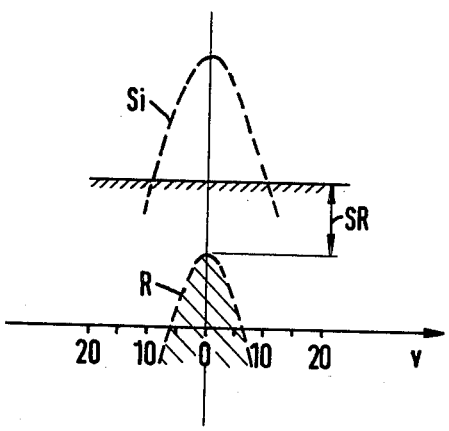
Figure 4A:
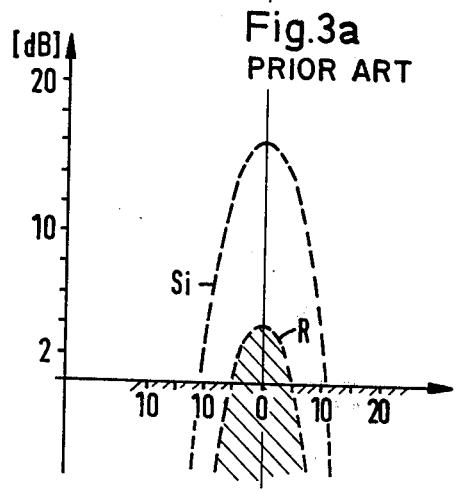
FIGS. 4a and 4b are plot diagrams which show, with the same variables plotted o the coordinate axes thereof, the echo level of the adjusting reflector for a test head with tandem technique (second depth zone) both for a conventional test head (FIG. 4a) and for a test head according to the invention (FIG. 4b)
Figure 4B:
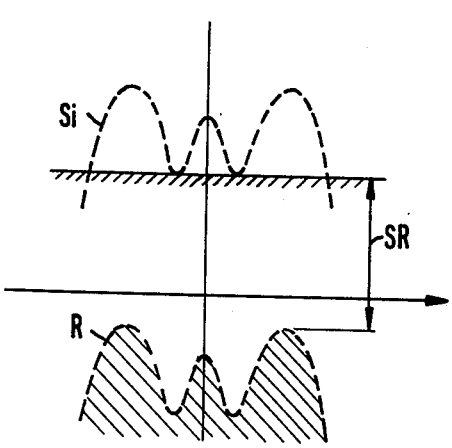

FIGS. 3a and 3b show once more the course of the sensitivity distributions according to FIGS. 1a and 2a, respectively, for the longitudinal transmit-recieve (TRL) technique of the first depth zone, placed in relation to corresponding plot diagrams of FIGS. 4a and 4b, which provide a comparison between a conventional two-oscillator test head (FIG. 4a) and a three-oscillator test head according to the invention (FIG. 4b) in tandem technique for the second depth zone. As is apparent, both of the sensitivity distributions which are formed by each of the transmitters, respectively, with the one receiver, overlap in the test head P2 according to the invention. On the resulting sensitivity distribution, which has a flatter course, sensitivity variations caused by interference phenomena are superposed. The test head P2 can also be used for the so-called longitudinal transmit-receive or TRL technique, wherein the outer oscillators S21 and S22 are driven simultaneously as transmitters and the oscillator E2 in the middle serves as the receiver. Such a three-oscillator test head P2 or also a four-or more-oscillator test head (not shown), however, can also be used for the tandem technique, a receiver test head E being associated with a transmitter test head SES, or a transmitter test head S being associated with a receiver test head ESE.

Figure 5:
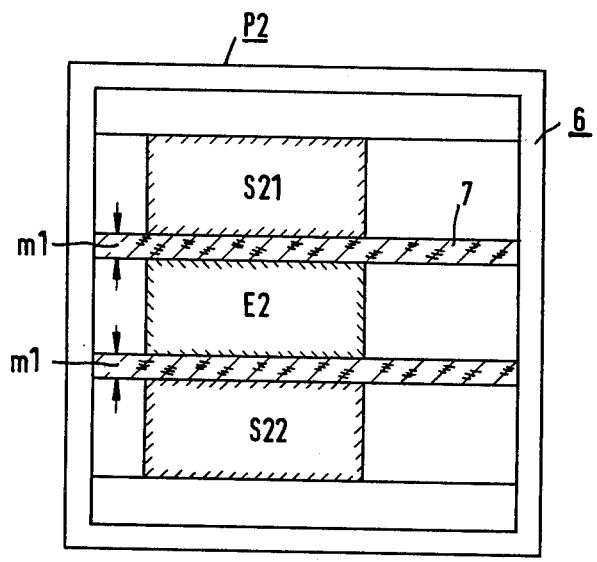
FIGS. 5 and 6 are top plan and side elevational views, respectively, partly in section, of structural details of the embodiment of a three-oscillator test head according to the invention.
Figure 6:
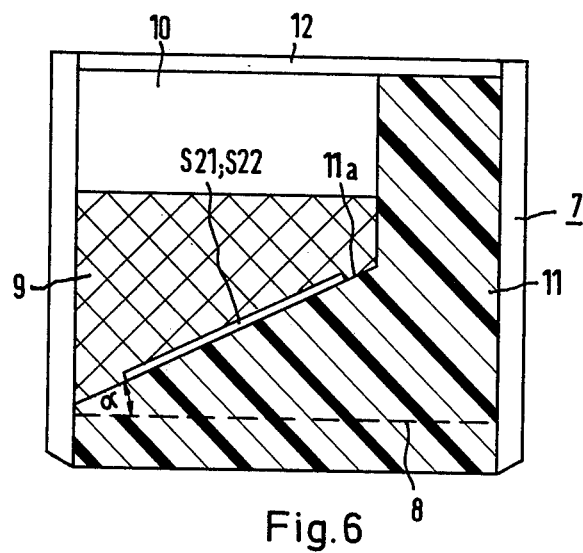

FIGS. 5 and 6 show structural details. In the housing 6, so identified as a whole, the individual crystals or oscillators for transmitters S21 and S22 and receiver E2 are disposed with mutually spaced-apart equal distances mL, gaps formed by these distances or spacings m1 being filled with cork 7 for acoustic separation. At the underside, runners 8 for sliding along the test track are located (FIG. 6), and the space not occupied by the crystals S21, E2, S22 is partly filled with damping material 9 on the side of the crystals facing away from the test surface, leaving a space 10 free for cable connectors and matching. On the crystal side facing toward the test surface, there is a wedge of plastic 11 with a support surface 11a which is inclined at an angle α to the horizontal and has the crystals S21, S22 and E2 fastened thereto. This angle α determines the insonification angle i.e. the angle at which the sound is transmitted. At the top of the test head P2, an identification plate 12 is embedded in the housing 6. Besides the longitudinal transmit-receive (TRL) technique, a preferred application of the three or more oscillator test head is ultrasonic testing by the TR technique (transmit-receive technique) with transverse waves. In addition, a further embodiment of the invention calls for the three- and more-oscillator test head to operate in accordance with a time-division multiplex method, as will be discussed hereinafter with reference to FIGS. 7, 7a, 8 and 9.

FIG. 7a shows diagrammatically a four-oscillator test head with the oscillators S21, E21, S22, E22 disposed serially i.e. one behind the other; in this case, also the function of the transmit oscillator crystals S21 and S22 are interchangeable with the function of the receiver crystals E21 and E22. In FIG. 7, the time t is plotted qualitatively along the abscissa, and the pulse amplitude I along the ordinate. In FIG. 7 the instantaneous plots or recordings of the time-division multiples operation are shown schematically, one below the other, and identified, respectively, as z1 and z4 (four instantaneous plots). During the time interval z1, the transmit crystal S22 emits a transmit pulse I1 and after a travel time u, a single echo signal e1 appears, within a probability range E, in the receive crystals E21 and E22, which are electronically switched in this case to receiving readiness. This means that the transmit pulse I1 has passed into the material to be examined or tested and, after reflection at the boundary surfaces, has arrived after the travel time u at the receiver crystals E21 and E22. The second plot z2 drawn below the first-mentioned plot z1 shows a transmit pulse I2 and an echo pulse e2 appearing on the pitcure screen of an oscilloscope after the travel time; in this case, the transmit oscillator crystal S22 was electronically cut off and the transmit crystal S21 was driven instead.

The plot recording z3, in turn, shows conditions corresponding to the plot recording z1 but shifted in time by a time period t3, and the plot recording z4, in turn, shows a transmit pulse I4, wherein electronically the same switching state prevails as during the instantaneous plot recording z2 (for reasons of space limitations, the plot diagram is discontinued at this juncture).

In the diagrammatic illustration of FIG. 9, the time-division multiplex method depicted in FIG. 7 is shown again in the third row or horizontal column identified by ZV4, the respectively driven crystals being indicated by crosses. Other possibilities of driving are shown in the rows or horizontal columns ZV2 and ZV3 located thereabove, which are self-explanatory.

In FIG. 8, the operation of the three-crystal test head shown in FIGS. 2a and 2b is explained again, according to the presentation of FIG. 9, in the lower horizontal column ZV5 for the case wherein all three oscillators are driven simultaneously. In the row or horizontal column thereabove, which is identified as ZV1, a time-division multiplex procedure for a three-oscillator test head is shown, wherein alternatingly the one or the other transmit oscillator is driven.

There are claimed:

1. Device for volumetric testing of pressure-vessel walls and pipes with a combined transmit-receive test head for scanning a sinuous test track having a given test-track spacing, comprising an oscillator unit including an oscillating crystal and a receive oscillating crystal having respective centers spaced apart a distance smaller than that of the test-track spacing so that the test head has a full width within which at least one additional oscillating crystal is accommodated, said additional oscillating crystal being paired with one of said transmit and receive oscillating crystals so as to form therewith another oscillating unit including a transmit oscillating crystal and a receive oscillating crystal having centers spaced apart a distance smaller than that of the test-track spacing, the distance between the crystals of both of said oscillator units being substantially equal, said additional oscillating crystal being a transmit crystal when said one crystal with which it is paired is a receive oscillating crystal, and being a receive oscillating crystal when said crystal paired therewith is a transmit oscillating crystal.

2. Device according to claim 1 wherein all of said crystals are of equal width.

3. Device according to claim 1 wherein the test head is a three-oscillator test head, and said crystals include two simultaneously driven outer transmit oscillating crystals and a receive oscillating crystal disposed therebetween.

4. Device according to claim 1 wherein the test head is a three-oscillator test head, and said crystals include two outer receive oscillating crystals and a transmit oscillating crystal disposed therebetween and driven so as to be simultaneously, received by said receive oscillating crystals.

5. Device according to claim 1 wherein the test head is at least a three-oscillator test head and is operatable for ultrasonic testing in a transmit-receive technique with lontigudinal waves.

6. Device according to claim 1 wherein the test head is at least a three-oscillator test head and is operatable for ultrasonic testing in a transmit-receive technique with transverse waves.

7. Device according to claim 1 wherein the test head is at least a three-oscillator test head and is operatable as a transmitter test head for ultrasonic testing in tandem technique, a receiver test head being associated with said transmitter test head.

* * * * *